(12) United States Patent
Zhang et al.

(10) Patent No.: US 11,141,525 B1
(45) Date of Patent: Oct. 12, 2021

(54) EAR-COVER STRUCTURE AND EAR IRRIGATION DEVICE

(71) Applicant: Ningbo Albert Novosino Co., Ltd., Zhejiang (CN)

(72) Inventors: Yonggui Zhang, Zhejiang (CN); Haibo Hu, Zhejiang (CN)

(73) Assignee: Ningbo Albert Novosino Co., Ltd., Ningbo (CN)

( * ) Notice: Subject to any disclaimer, the term of this patent is extended or adjusted under 35 U.S.C. 154(b) by 0 days.

(21) Appl. No.: 17/153,850

(22) Filed: Jan. 20, 2021

(30) Foreign Application Priority Data

Oct. 17, 2020 (CN) .......................... 202022319622.4

(51) Int. Cl.
*A61M 3/02* (2006.01)

(52) U.S. Cl.
CPC ... *A61M 3/0287* (2013.01); *A61M 2210/0662* (2013.01)

(58) Field of Classification Search
CPC ........ A61K 9/0046; A61M 2210/0662; A61M 3/0283; A61M 3/0279; A61M 25/00; A61M 35/003; A61M 1/0058; A61M 2205/502; A61M 2209/088; A61M 3/0208; A61M 3/0212; A61M 3/022; A61M 3/0275; A61M 3/0287; A61F 11/006

See application file for complete search history.

(56) References Cited

U.S. PATENT DOCUMENTS

| | | | |
|---|---|---|---|
| 8,187,236 B1 * | 5/2012 | French | A61M 3/025 604/275 |
| 10,420,877 B2 * | 9/2019 | Diwan | A61M 1/0058 |
| 10,758,666 B1 * | 9/2020 | Schultz | A61M 3/0262 |

* cited by examiner

*Primary Examiner* — Brandy S Lee

(57) ABSTRACT

The present application discloses an ear-cover structure and an ear irrigation device. The ear-cover structure includes a cover configured with a containing space with an opening configured at a side of the containing space, a liquid collecting portion extending outwards from the bottom of the cover, and an injection port configured on the cover and communicating with the containing space. The medium collected in the containing space flows through the liquid collecting portion and is discharged from a leakage port to the external environment.

10 Claims, 12 Drawing Sheets

EAR-COVER STRUCTURE AND EAR IRRIGATION DEVICE

CROSS-REFERENCE TO RELATED APPLICATION

This application claims the priority benefit of China application No. 202022319622.4 filed on Oct. 17, 2020. The entirety of the above-mentioned patent application is hereby incorporated by reference herein and made a part of this specification.

BACKGROUND

Technical Field

The present disclosure relates to the field of medical equipment, and more particular to an ear-cover structure and an ear irrigation device.

Description of Related Art

The process for cleaning ear canal out helps to stay the ear clean, and is able to reduce the accumulation of secretions in the ear canal, which may affect hearing ability or cause chronic otitis externa and other diseases. In conventional, cleaning processes for the ear canal is adopted by a flushing process. A syringe is adopted to spray saline into the ear canal for flushing, and a basin is provided to hold the used saline with ear canal secretions flowing downstream from the ear.

Regarding the mentioned technologies related, it is believed that, when the ear canal cleaning process is conducted, the medical staff has to hold the syringe in one hand, and pay attention for finding the position of the sprayed liquid, then keeping the other hand to hold the basin and making sure where the position of the cleaning fluid flowing downstream from the ear is as well. During above cleaning progress, the medical staff is distracted from serious medical care operations because he/she has to pay attention on multiple items at the same time, which is significantly inconvenient and disadvantageous.

SUMMARY

In order to facilitate the ear canal cleaning process, the present application provides an ear-cover structure.

An ear-cover structure provided by this application adopts the following technical solutions: an ear-cover structure, includes a cover having a top wall and a peripheral side wall, the top wall and the peripheral side wall enclosing together to define a containing space with a substantially elliptical opening on one side of the containing space; and a liquid collecting portion, configured at one end located at a long axis of the substantially elliptical opening, extending from the cover in a direction away from the containing space, and communicating with the containing space; wherein, the cover is provided with: an injection port opened at the approximate center of the top wall of the cover and communicating with the containing space; and a leakage port configured at one end of the liquid collecting portion away from the containing space and communicating with the containing space, when the ear-cover structure is in use, the fluid collected in the containing space flows through the liquid collecting portion and is discharged to the external environment from the leakage port.

By adopting the above technical solution, before the cleaning progress for the ear canal is conducted, the containing space of the cover is used to cover the entire ear at first. The cover is configured with the injection port for adopting the nozzle of the syringe to penetrate into the cover. The size of the cover and the location of the injection port are selected based on the normal distributing position of ordinary human ear canal, so as to realize the alignment between the injection port and the ear canal. Therefore, the nozzle of the syringe is able to be aligned with the ear canal efficiently after the nozzle is inserted from the injection port. Under the action of gravity, the cleaning liquid flowing out from the ear canal is collected in the liquid collecting portion and discharged from the leakage port of the liquid collecting portion to the external environment. The advantage of fixed-point drainage is realized thereon so that there is no necessary for the medical staff to hold the basin and observe the flowing path of the downstream cleaning liquid at the same time anymore, which is convenient and advantageous for the operation of cleaning entire ear canal.

Preferably, a catheter with one end extending toward the opening is provided in the cover, and the catheter is configured with a guide channel communicating with the injection port.

By adopting the above technical solution, after the cover is conducted to cover the ear, the catheter is able to extend to the position of the ear hole. The nozzle of the syringe is conducted to enter into the guide channel from the injection port, and the axis of the syringe nozzle is kept relatively horizontal through the guide channel, which makes the alignment between the injection port and the ear canal being more accurate. In the meantime, because the catheter is also capable of sustaining a certain weight of the syringe nozzle, the operating intensity of the medical staff for hand-holding the syringe is appropriately reduced, which complies with needs of the ergonomics designs more in above spray flushing process.

Preferably, the inner wall of the guide channel is provided with at least one protrusion blocker.

By adopting the above technical solution, after the nozzle of the injector is conducted to enter into the guide channel, the protrusion blocker is capable of increasing the friction force with the nozzle surface, and the nozzle is able to be pressed against the nozzle therefore, which reduces the trembling shakes and rotating movements of the nozzle in the guide channel, so as to improve the fixed ability for the nozzle, and further raise the accuracy and stability of the flushing operation during the spray cleaning process.

Preferably, a hose connector, extending from the leakage port, and provided with a leak channel connecting with the leakage port, is further included.

By adopting the above technical solution, the cleaning liquid flows into the hose connector from the leakage port, and is discharged to the outside environment through the leakage channel, so as to improve drainage effect of the cleaning liquid from a certain direction. Synchronously, a hose is able to be connected with the external portion of the hose connector, and the hose is able to be directly connected to the basin thereby. Accordingly, the flexibility of the cleaning process for the ear canal is improved.

Preferably, the cover is provided with a skirt portion around the outer edge of the opening.

By adopting the above technical solution, the configuration of the skirt portion enlarges the fitting area of the cover when the cover is conducted to cover on the side face of an individual, so as to improve the comfort of the cover entirely for covering the man face. Moreover, the sealing ability of the cover is increased at the same time so as to reduce the leaking of the cleaning liquid from the opening. Due to enlarged contacting area at the opening, the skirt portion is capable of holding the shape of the entire cover accordingly, so as to reduce the collapse of the cover at the opening. Therefore, the stability of ear canal cleaning process becomes better accordingly.

Preferably, the skirt portion is provided with a curve-shaped sealing surface, and the vertical distance of a forward projection of the sealing surface to the vertical plane from the highest point position to the lowest point position increases gradually.

By adopting the above technical solution, after the cover is fitted with the ear, the sealing surface is fitted with the man face by an external pressing force. The curve-shaped design of the sealing surface is able to better comply with the curve of the man face from the ear to the chin position so as to improve the sealing ability of the cover after fitting with the man face.

Preferably, the cover includes a top wall and a peripheral side wall, the top wall and the peripheral side wall enclose together to define the containing space, the cover is provided with a pressing area protruding toward one side of the containing space, and the pressing area is configured between the peripheral side wall and the top wall.

By adopting the above technical solution, after the cover is conducted to cover the ears, it's necessary for the cover to be pressed by the external force to ensure the fitness between the cover body and the man face. Normally, the external force is a specific force applied to the cover by a man hand. The setting of the pressing area is more ergonomic for people's fingers to press the pressing area and force on it, and the pressing area is configured between the peripheral side wall and the top wall. Because the above position is located at a connection position between the peripheral side wall and the top wall, it has a certain structure strength so as to make sure the deformation of the cover is limited enough to avoid the offset of the injection port during the pressing process.

Preferably, the cover is further provided with an air vent communicating with the containing space.

By adopting the above technical solution, the opening of the air vent is able to communicate the containing space with the external environment so as to avoid a negative pressure (the difference of the pressure between the inside of the cover and the outside of it) generated in the cover during the ear canal cleaning process, which prevents the cleaning liquid from being discharged. In the meantime, the air vent is able to realize an air exchanging between inside and outside of the cover as well, so as to reduce the problem of excessive temperature existing inside the cover thereby.

Preferably, a connector is further provided, and two ends of the connector are respectively connected with the cover.

By adopting the above technical solution, after the cover is conducted to cover the ear, the connector is implemented to fix the head of the human body, and, accordingly, there is no necessary to fit the cover with the face by an external force so as to make the ear canal cleaning progress being more convenient.

In order to facilitate the ear canal cleaning progress, the present application further provides an ear irrigation device.

The ear irrigation device provided in this application adopts the following technical solutions: an ear irrigation device, includes a syringe; a nozzle, connected to the syringe; and the above ear-cover structure, with one end of the nozzle being able to extend into an injection port.

By adopting the above technical solution, before irrigation process of the ear canal is conducted, the containing space of the cover is conducted to cover the entire ear, and the cover is provided with an injection port capable of being penetrated by the nozzle. The size of the cover and the location configuration of the injection port are configured based on the normal distributing position of ordinary human ear canal, so as able to realize the alignment between the injection port and the ear canal to make the nozzle is able to be aligned with the ear canal efficiently after the nozzle is inserted from the injection port. The cleaning fluid is injected into the nozzle then is sprayed from the nozzle through the syringe. The irrigation liquid flows out from the ear canal and is collected into the liquid collecting portion under the action of gravity. Furthermore, the irrigation liquid is discharged from the leakage port of the liquid collecting portion to the external environment thereafter, so as to realize the effect of fixed-point drainage accordingly. There is no necessary for the medical staff to hold the basin and observe the path of the downstream cleaning liquid at the same time, which is convenient and advantageous for the progress of cleaning entire ear canal.

In summary, this application has at least one of the following beneficial technical effects:

(1) The ear-cover structure is configured as an auxiliary part during the ear canal cleaning process. The nozzle is introduced through the opening of the injection port to achieve the effect for aligning the nozzle with the ear canal efficiently. Meanwhile, the configuration for the opening of the leakage port makes the cleaning fluid and earwax to be discharged from a fixed position so as to simplify the entire ear canal cleaning progress.

(2) The introduction of the nozzle and the positioning of the nozzle are realized by configured the catheter in the cover and the protrusion blocker in the guide channel. Therefore, it is better improve the positioning accuracy of the nozzle. In addition, since the guide channel is provided with a certain length and capable of holding the weight of the nozzle, by adopting with the pressing area configured on the outer surface of the cover, the entire ear canal cleaning progress becomes more ergonomic.

(3) The skirt portion provided at the opening increases the corresponding area fitted with the side face, so that the sealing surface formed along with the edge of the skirt portion is enhanced with better sealing ability, which is able to reduce the leakage of cleaning fluid from the opening. At the same time, the sealing surface is configured with arc shape according to the curve of the man face for better improving the fitness between the cover and the man face. The opening of the air vent is capable of raising the air exchange efficiency between the inside of the cover and the outside environment by avoiding the negative pressure to be generated inside the cover, and further avoids the case that, because the air flow in the cover is not fluent, the temperature inside the cover is getting excess high.

(4) The whole cover is able to be fixed with the man head by the configuration of the connecting piece, and the enforcement of external force on the cover body for ensuring the fitness between the cover and the man face is no longer necessary thereafter.

DESCRIPTION OF THE EMBODIMENTS

This application will be further described in detail below with reference to FIGS. 1-12.

It should be noted that when an element is referred to as being "fixed to" another element, it can be directly on the other element or a central element may also exist. When an element is considered to be "connected" to another element, it can be directly connected to the other element or an intermediate element may also exist. The terms "vertical", "horizontal", "left", "right" and similar expressions used herein are for illustrative purposes only, and do not mean it is the only implementation.

Unless otherwise defined, all technical and scientific terms used herein have the same meaning as commonly understood by those skilled in the technical field of the present invention. The terms used in the specification of the present invention herein are only for the purpose of describing specific embodiments, and are not intended to limit the present invention. The term "and/or" as used herein includes any and all combinations of one or more related listed items.

Figure 1:
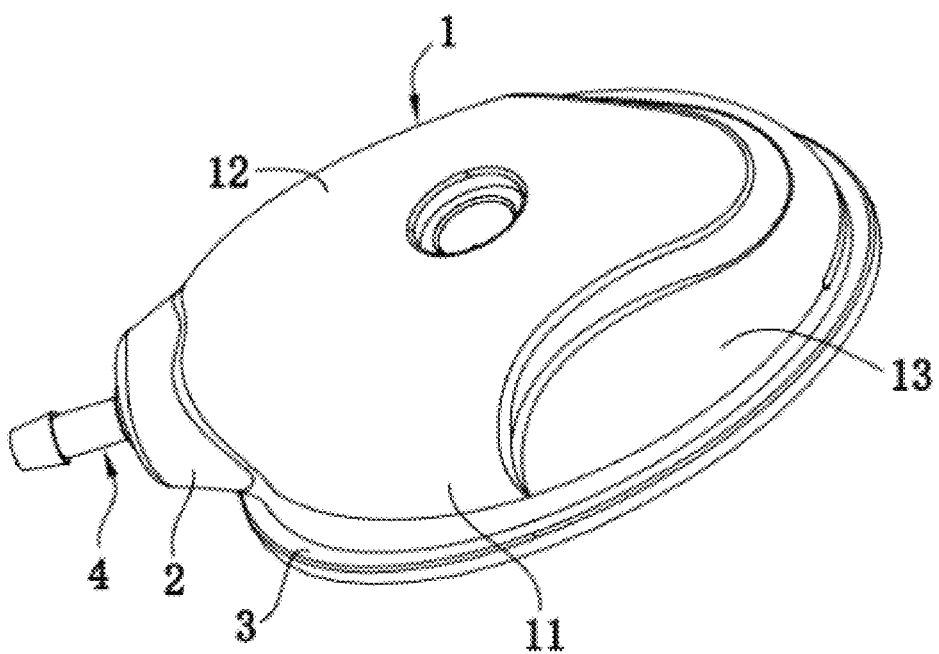
FIG. 1 is a schematic diagram of the ear-cover structure in the first embodiment.
Figure 2:
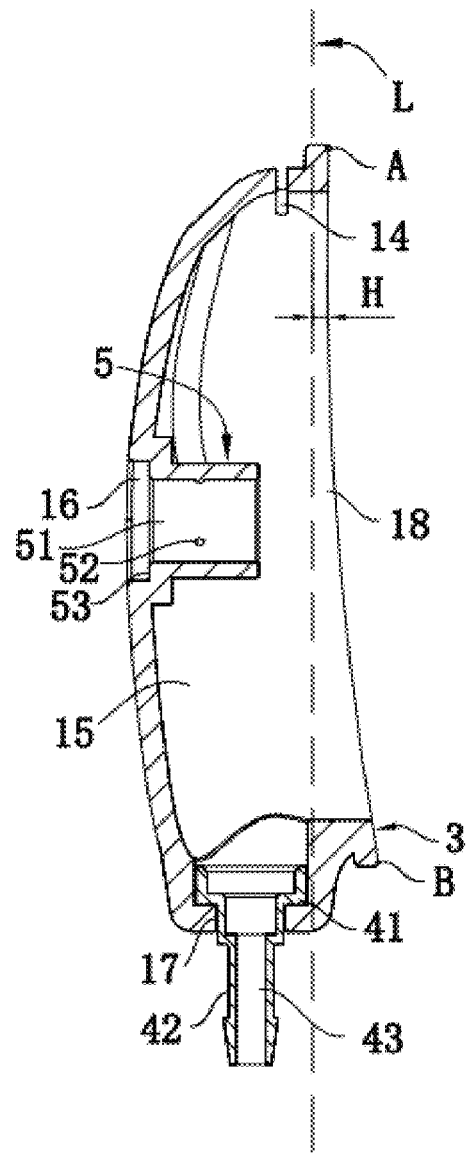
FIG. 2 is a cross-sectional view of the ear-cover structure in the first embodiment.

Embodiment 1. Referring to FIG. 1 and FIG. 2 together, an ear-cover structure including a cover 1, a liquid collecting portion 2 and a hose connector 4 is disclosure in this embodiment.

The cover 1 is in the shape state of a basin, and provided with a peripheral side wall 11 and a top wall 12. The peripheral side wall 11 and the top wall 12 are enclosed together to define a containing space 15. The containing space 15 is configured with an opening 18. The opening 18 is configured at the side opposite to the top wall 12 of the containing space 15, and the containing space 15 contains a volume capable of covering a man ear 10.

An injection port 16 is configured at the top wall 12 of the cover, and a catheter 5 is provided at the inner wall of the cover 1, one end of the catheter 5 extends toward one side of the opening 18, and the catheter 5 is provided with a guide channel 51 communicating with the injection port 16. A limiting surface 53 is provided on one surface of an end of the catheter 5 away from the opening 18. Furthermore, at least one protrusion blocker 52 is provided at the inner wall of the guide channel 51 as well. In this embodiment, three protrusion blockers 52 are provided, which are evenly distributed on the guide channel 51 along the circumferential direction.

The liquid collecting portion 2 is provided on the peripheral side wall 11 of the cover 1 and is integrated with the cover 1 as an integral structure. One end of the liquid collecting portion 2 extends radially from the side of the peripheral side wall 11 opposite to the cover body 1. A leakage port 17 is configured in the liquid collecting portion 2, and the leakage port 17 and the injection opening 16 both communicate the containing space 15. When it is in use, the cleaning liquid flows through the liquid collecting portion 2 and be discharged from the leakage port 17 into the external environment.

The hose connector 4 is provided to connect on the liquid collecting portion 2 and includes a connector 41 and a tube section 42. In this embodiment, the leakage port 17 is a countersunk opening, the connector 41 and the leakage port 17 are clamped together, and the connecting surface between the connector 41 and the leakage port 17 is sealed with each other further by gluing process. One end of the tube section 42 extends from the leakage port 17 and is specifically provided for the connection of a hose. The entire hose connector 4 is provided with a leakage channel 43 connecting with the leakage port 17. In particular, the cover 1 is made of soft material, such as rubber or silicone, which is more comfortable when it fits with the human face 20. The hose connector 4 is made of hard material, such as hard rubber, which is more suitable for the connection of the hose, so that the connection between the hose connector 4 and the hose becomes solid and the chance for the disconnection between the hose connector 4 and the hose is reduced accordingly.

The cover 1 is also provided with a skirt portion 3 at the position of the opening 18, the skirt portion 3 is configured around the outer edge of the opening 18, and one end surface of the skirt portion 3 is a sealing surface. A vertical plane L is defined as shown in FIG. 2. After that, when the tube section 42 faces vertically downwards, the cover 1 is in a forward projection state, the vertical distance H between the sealing surface and the vertical plane L gradually increases from the highest point A to the lowest point B. In the other word, the sealing surface is arc-shaped.

The cover 1 is also configured with an air vent 14 communicating with the containing space 15. The air vent 14 is implemented to ensure that the air pressure in the containing space 15 is consistent with the air pressure of the external environment. In this embodiment, the air vent 14 is configured on the side of the peripheral side wall 11 opposite to the leakage port 17 to reduce the possibility of discharging the cleaning liquid from the air vent 14.

Figure 3:
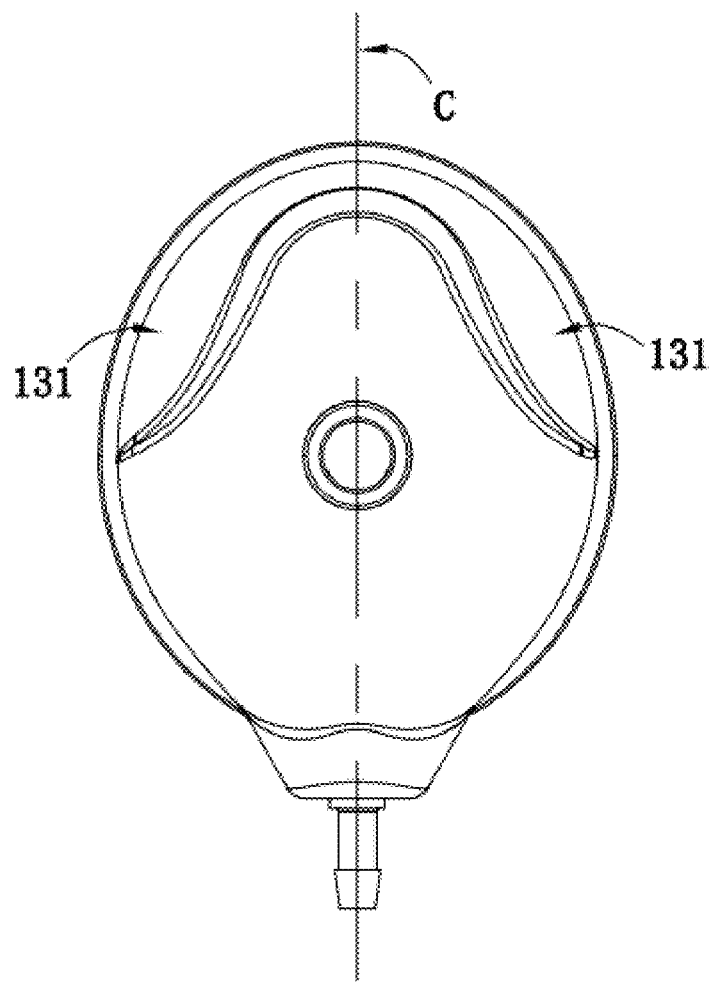
FIG. 3 is a front view of the ear-cover structure of the first embodiment.

Referring to FIG. 1 and FIG. 3 together, the outer surface of the cover 1 is provided with a pressing area 13 protruding toward one side of the containing space 15. The protrusion of the pressing area 13 is provided for ensuring that the pressing area 13 has enough thickness, the thickness of the entire cover 1 is relatively uniform thereby, so as to reduce the overall deformation of the cover 1. The pressing area 13 is provided on a side of the cover 1 away from the liquid collecting portion 2 and at a connection position between the peripheral side wall 11 and the top wall 12. A vertical plane C of the cover body 1 is defined as shown in FIG. 3, the pressing area 13 is configured with two acupressure portions 131 symmetrical to the vertical plane, which are provided to implement the pressure force on the cover 1 by pressuring the pressing area 13 using a human finger. Because the peripheral side wall 11 contains with a certain height, the connection portion between the top wall 12 and the peripheral side wall 11 is shaped as a corner-shape portion, and the corner-shape portion is with relatively higher sustaining capability. Under above, when at least one of the acupressure portions 131 is stressed, the deformation of the cover 1 caused by the stressing operation is limited accordingly.

Figure 4:
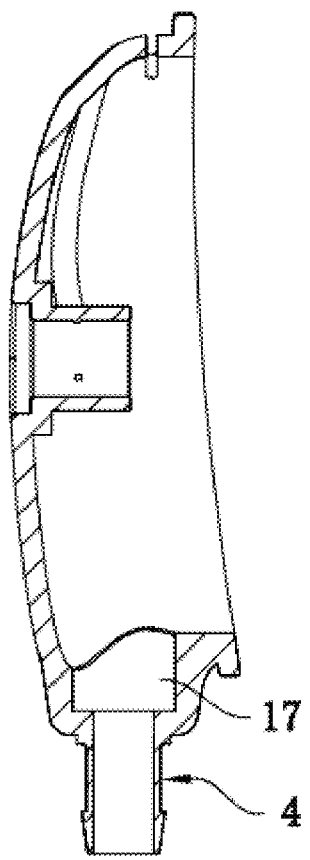
FIG. 4 is a schematic diagram of the ear-cover structure in the second embodiment.

Embodiment 2. Referring to FIG. 4, this embodiment discloses an ear-cover structure. The difference from the first embodiment is that the hose connector 4 is integrally provided with the liquid collecting portion 2 as an integral structure.

Figure 5:
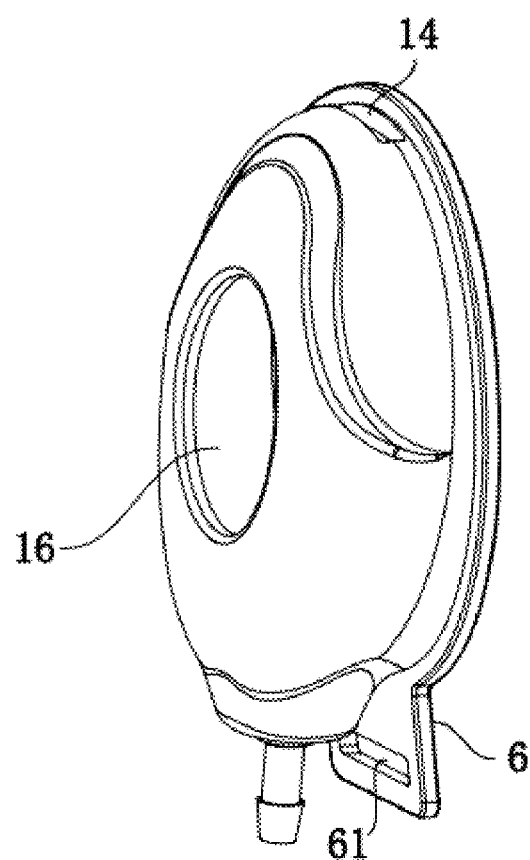
FIG. 5 is a schematic diagram of the ear-cover structure without the connecting piece in the third embodiment.
Figure 6:
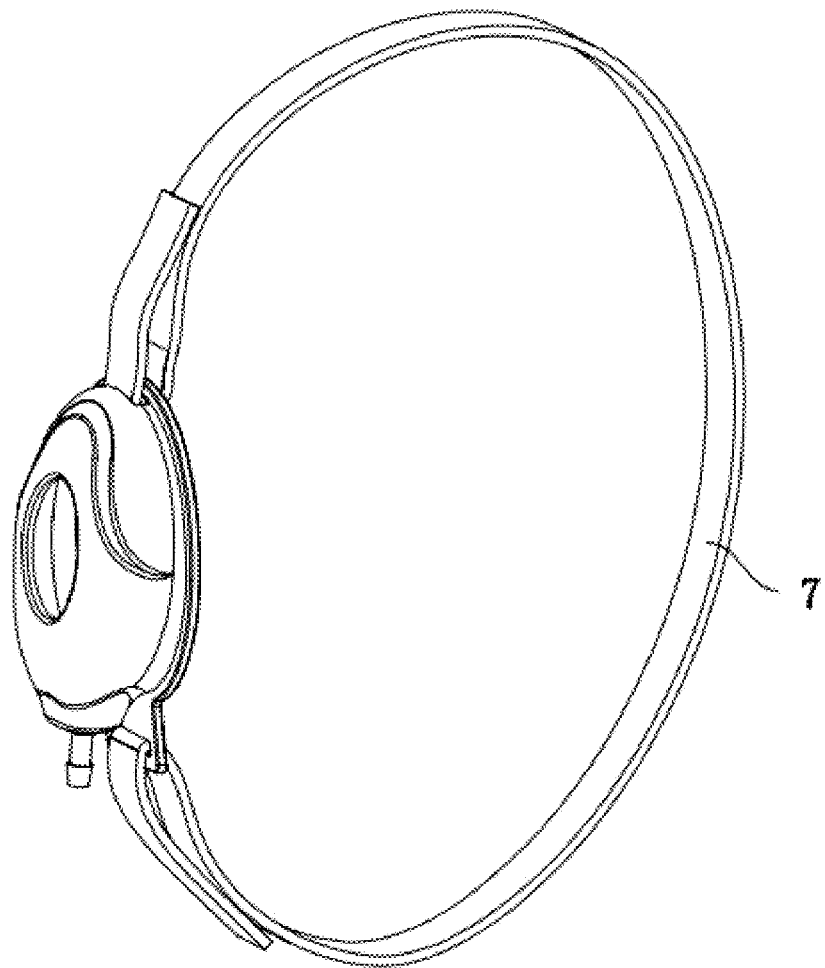
FIG. 6 is a schematic diagram of the ear-cover structure with the connecting piece in the third embodiment.

Embodiment 3. Referring to FIGS. 5 and 6 together, this embodiment discloses an ear-cover structure. The difference from the first embodiment is that it further includes a connecting piece 7, and an extending portion 6 is provided at the skirt portion 3 as well. A through hole 61 is configured on the extending portion 6, and one end of the connecting piece 7 is penetrated through the through hole 61 to connect to the extending portion 6, and the other end of the connecting piece 7 is penetrated through the air vent 14 to connect to the cover body 1, so as to realize the fixation between the connecting piece 7 and the cover body 1. In this embodiment, the connecting piece 7 is an elastic band, and certainly, a binding member with elastic deformation ability such as an elastic band or a rubber band are both able to be implemented.

Figure 7:
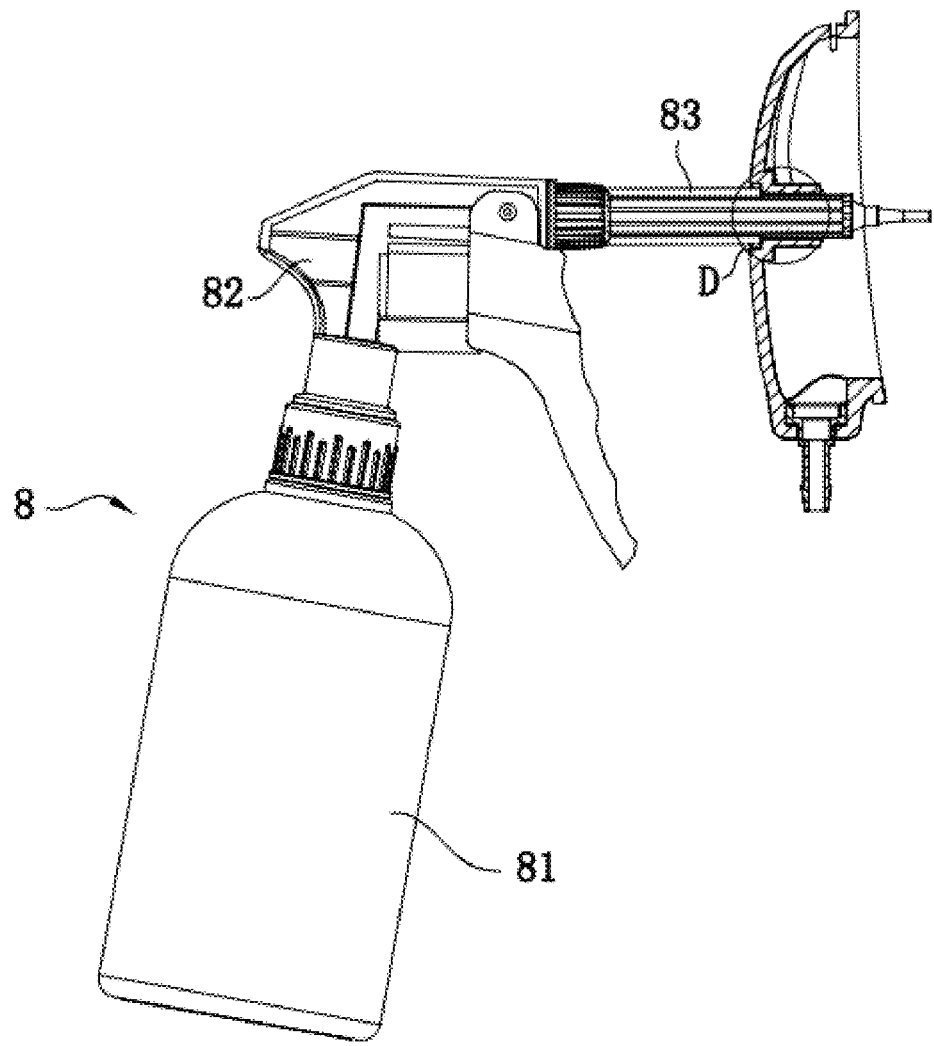
FIG. 7 is a schematic diagram of the structure of the ear irrigation device in the fourth embodiment.
Figure 8:
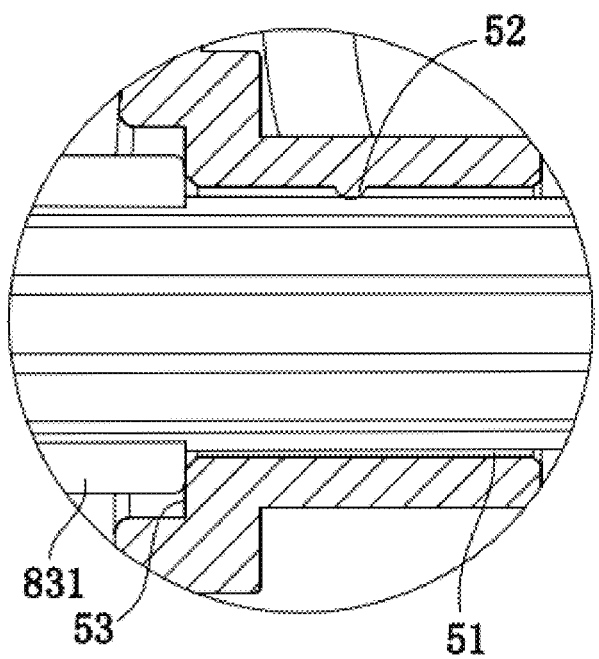
FIG. 8 is an enlarged view diagram of portion D in the FIG. 7.

Embodiment 4. Referring to FIGS. 7 and 8 together, this embodiment discloses an ear irrigation device 10, which includes a syringe 8 and the ear-cover structure disclosed in the first or second embodiment. The syringe 8 includes a container 81 for containing cleaning liquid and a spray injector 82 connected to the container 81, and one end of the spray injector 82 is connected with a nozzle 83.

One end of the nozzle 83 is able to extend from the injection port 16 through the catheter 5 into the containing space 15. At least one limit rod 831 is provided in a circumferential arrangement on the outer wall of the nozzle 83. The limit rod 831 is with a certain length but shorter than the length of the nozzle 83 in total. After the nozzle 83 is extended into the containing space 15, the end portion of the limit rod 831 is able to abut on the limiting surface 53 to realize stroke limitation. Meanwhile, the outer wall of the nozzle 83 is configured in a spline shape, and the protrusion blocker 52 abuts against the outer wall of the nozzle 83 to limit the relative position between the nozzle 83 and the containing space 15 thereon in the circumferential and radial directions respectively.

Figure 9:
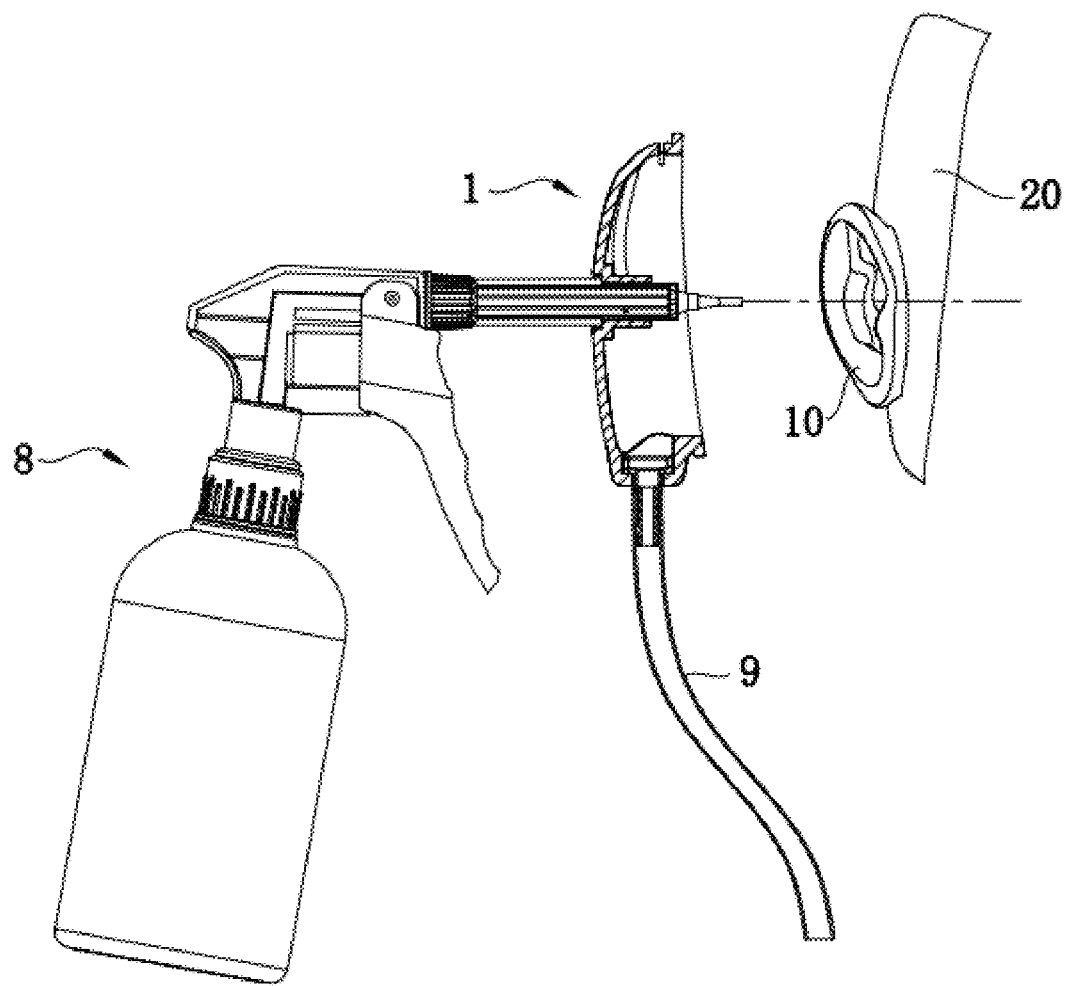
FIG. 9 is a diagram of the use state of the ear irrigation device in the fourth embodiment.
Figure 10:
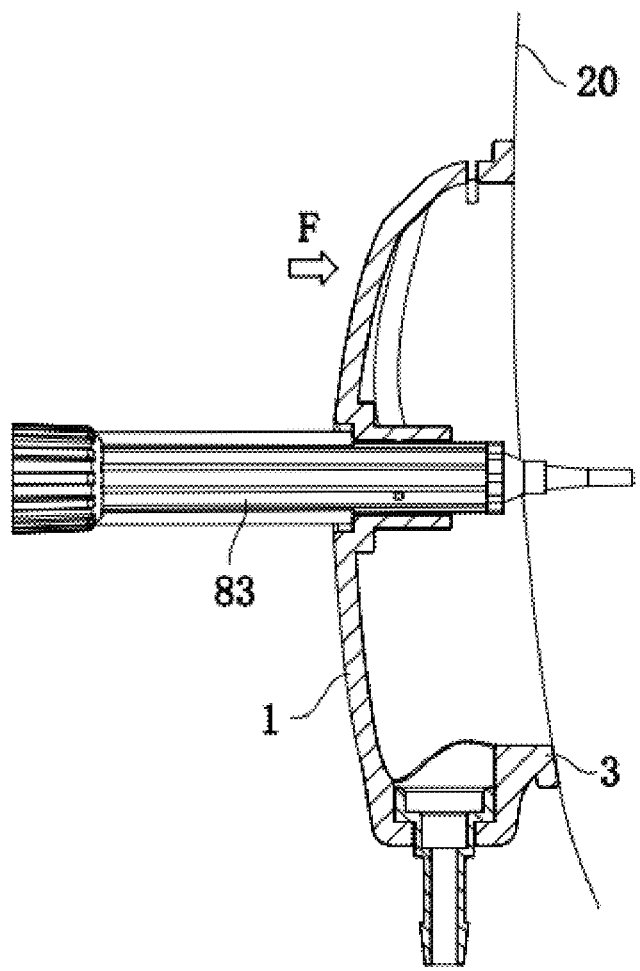
FIG. 10 is a schematic diagram shown the state of the cover and a man face under the external force F in the fourth embodiment.

Referring to FIG. 9 and FIG. 10 together, when the disclosed ear irrigation device is in use, the angle of the cover 1 is adjusted in advance so that the hose connector 4 faces vertically downwards accordingly after above adjustment, and at the same time, the hose 9 is connected with the hose connector 4 externally, with one end of the hose 9 extending into the basin. Thereafter, the nozzle 83 of the syringe 8 is extended into the injection port 16 until the end portion of the limit rod 831 abuts on the limit surface 53, the cover 1 and the syringe 8 are displaced together finally, and the man ear 10 is completely covered by the cover 1. The skirt portion 3 is attached to fit the man face 20, and the spray injector 82 is operated to spray the cleaning liquid upon from the container 81 and into the man ear 10 through the nozzle 83 for irrigation. The cleaning liquid and the earwax are discharged to the outside through the hose 9 by following the flow of the cleaning liquid. The ear irrigation device is able to be operated with one hand only. Only by the implementation of the nozzle 83 of the syringe 8 acting on the cover 1, the fitness between the cover 1 and the human face 20 is kept accordingly.

In addition, the cleaning process is more in line with ergonomics concept. Human fingers act on the finger pressing area 131 to conduct a force F. The finger pressing area 131 is provided on the side of the cover 1 away from the liquid collecting portion 2, and the catheter 5 is with enough length capable of sustaining the nozzle in a certain degree. Under regular operation conditions, by holding the ear-cover with one hand and the syringe 8 with the other hand, when the force F is gradually increased, the fitness between the skirt portion 3 and the man face 20 is enhanced accordingly, and the more solid the fitness between the skirt portion 3 and the man face 20 is, the less the weight of the syringe 8 is hold by the other hand of the user, so as to reduce the intensity for a long time operation during the spraying process.

Figure 11:
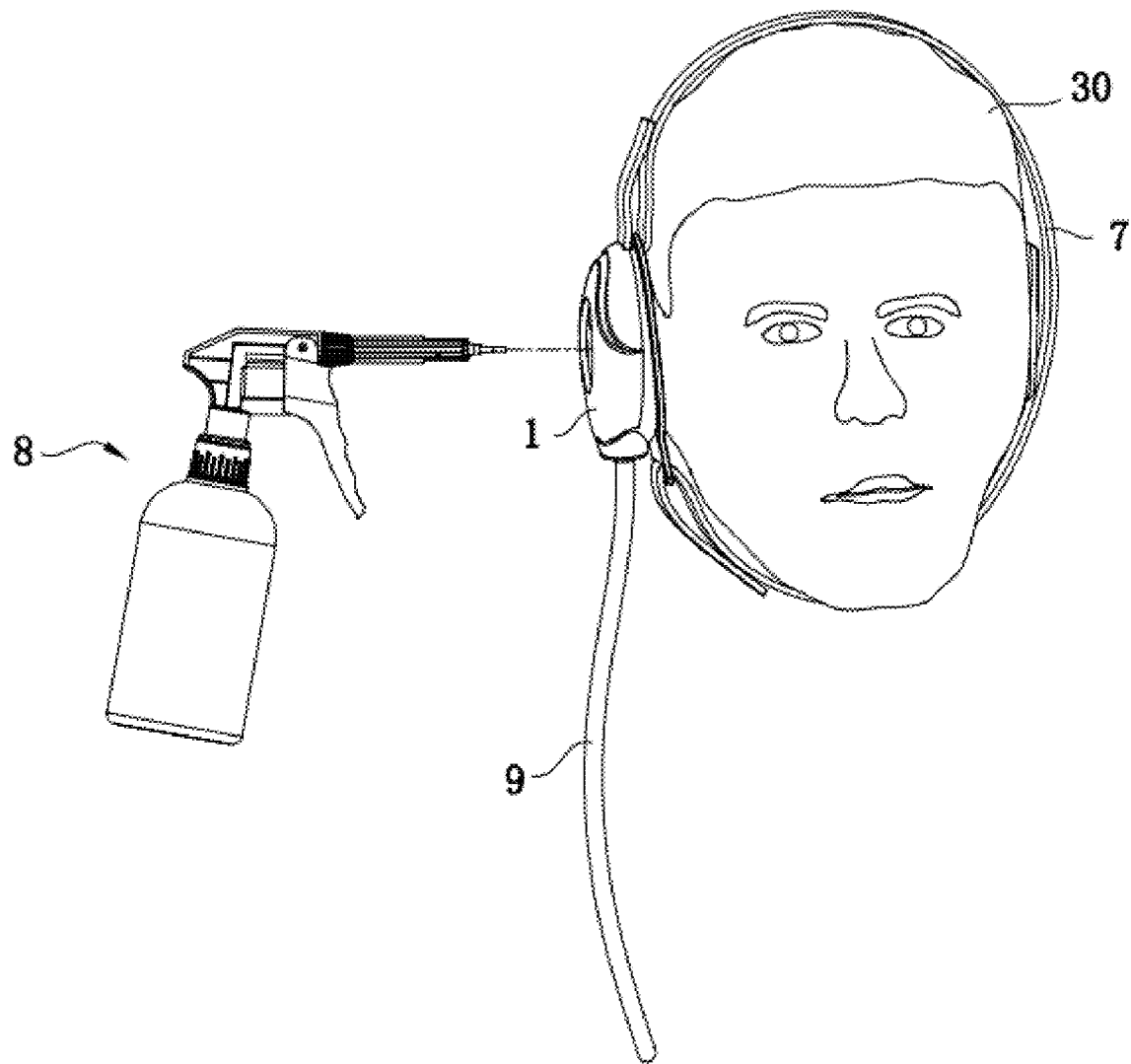
FIG. 11 is a diagram of the use state of the ear irrigation device in the fifth embodiment.

Embodiment 5. Referring to FIG. 11, this embodiment discloses an ear irrigation device. The difference from the fourth embodiment is that the ear-cover structure in the third embodiment is adopted in this embodiment.

When the ear irrigation device is in use, the cover 1 is conducted to cover the man ears 10 in advance, and the cover 1 is then fixed with the human head 30 through the connector 7, so as to realize the fixation between the cover 1 and the head 30. The disclosed cleaning process is able to be performed only by extending the nozzle 83 of the syringe 8 into the containing space 15.

Figure 12:
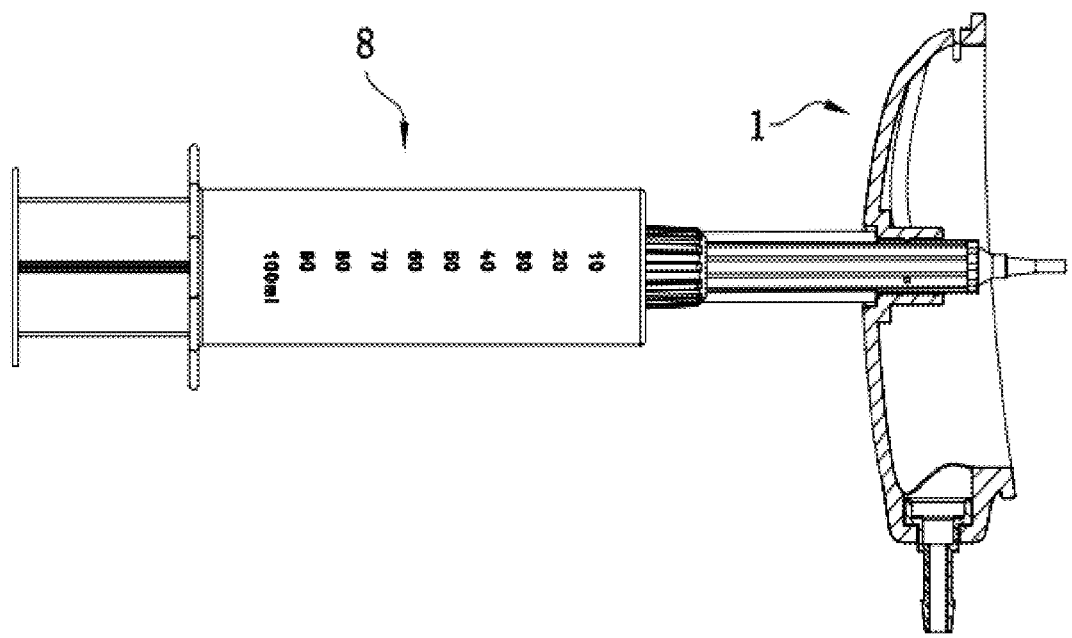
FIG. 12 is a schematic diagram of the structure of the ear irrigation device in the sixth embodiment.

Embodiment 6. Referring to FIG. 12, this embodiment discloses an ear irrigation device. The difference of this embodiment from the fourth and fifth embodiments is about the selection for the syringe 8. In this embodiment, a conventional syringe is used as the syringe 8.

Certainly, in the fourth to sixth embodiments, the syringe 8 is able to be selected from a manual syringe or an electric syringe, and it is not limited to the selection for the syringe 8 in this application, as long as it is able to meet the spraying process of cleaning liquid.

The above are the preferred embodiments of this application, and the scope of protection of this application is not limited accordingly. Therefore: all equivalent changes made in accordance with the structure, shape, and principle of this application shall be covered by the scope of protection of this application inside.

What is claimed is:

1. An ear-cover structure, comprising:
   a cover, provided with a top wall and a peripheral side wall, the top wall and the peripheral side wall enclosing together to define a containing space with a substantially elliptical opening on a side of the containing space; and
   a liquid collecting portion, configured at one end located at a long axis of the substantially elliptical opening, formed by an extension of the cover in a direction away from the containing space, and communicating with the containing space; wherein one end of the liquid collecting portion extends radially from the side of the peripheral side wall opposite to the cover,
   wherein, the cover is provided with:
   an injection port, configured at the approximate center of the top wall of the cover and communicating with the containing space; and
   a leakage port, configured at one end of the liquid collecting portion away from the containing space and communicating with the containing space,
   when the ear-cover structure is in use, the fluid collected in the containing space flows through the liquid collecting portion and is discharged to the external environment from the leakage port.

2. The ear-cover structure according to claim 1, wherein a catheter with an end extending toward the opening is provided in the cover, and the catheter is configured with a guide channel communicating with the injection port.

3. The ear-cover structure according to claim 2, wherein an inner wall of the guide channel is provided with at least one protrusion blocker.

4. The ear-cover structure according to claim 1, wherein a hose connector is further provided, and the hose connector is extended from inside of the leakage port and provided with a leak channel communicating with the leakage port.

5. The ear-cover structure according to claim 1, wherein the cover is provided with a skirt portion around the outer edge of the opening.

6. The ear-cover structure according to claim 5, wherein the skirt portion is provided with a sealing surface shaped in curve-shape, and the vertical distance of a forward projection of the sealing surface to the vertical plane from the highest position to the lowest position increases gradually.

7. The ear-cover structure according to claim 1, wherein the cover is provided with a top wall and a peripheral side wall, the top wall and the peripheral side wall enclose together to define the containing space, the cover is provided with a pressing area protruding toward one side of the containing space, and the pressing area is configured between the peripheral side wall and the top wall.

8. The ear-cover structure according to claim 1, wherein the cover is further configured with an air vent communicating with the containing space.

9. The ear-cover structure according to claim 1, wherein a connecting piece is further provided, and two ends of the connecting piece are respectively connected with the cover.

10. An ear irrigation device, comprising:
a syringe;
a nozzle, connecting to the syringe, and
an ear-cover structure according to claim 1, with an end of the nozzle being able to extend into the injection port.

* * * * *